United States Patent
Schenck et al.

Patent Number: 5,705,014
Date of Patent: Jan. 6, 1998

[54] CARBON FIBER MAGNETIC RESONANCE COMPATIBLE INSTRUMENTS

[75] Inventors: John Frederick Schenck, Schenectady; Kenneth William Rohling, Burnt Hills, both of N.Y.

[73] Assignee: General Electric Company, Schenectady, N.Y.

[21] Appl. No.: 620,143

[22] Filed: Mar. 22, 1996

[51] Int. Cl.$^6$ .................................................. B32B 31/00
[52] U.S. Cl. .............. 156/272.4; 156/242; 156/244.23; 156/245; 156/272.2; 156/279; 128/653.2
[58] Field of Search .................... 156/242, 244.23, 156/245, 272.2, 272.4, 279; 128/653.2

[56] References Cited

PUBLICATIONS (Book) Chapers 1 and 6 of "Carbon Fibers, Formation, Struicture and Properties" by L.H. Peebles, CRC Press, Boca Raton, Florida (1995) pp. 1 & 59–94).
Proceedings of the Society of Magnetic Resonance, "Carbon Fiber Biopsy Cannulas for MR–Compatible Neurosurgical Procedures" by J.F. Schenck, K.W. Rohling, T.M. Moriarity, E. Alexander, II, F.A. Jolesz, Nice, France, Aug. 19–25, 1995, vol. 2

*Primary Examiner*—Richard Weisberger
*Attorney, Agent, or Firm*—Lawrence P. Zale; Marvin Snyder

[57] ABSTRACT

Instruments are constructed of a carbon fiber material optionally doped with a doping agent such as iron oxide, the instrument having a magnetic susceptibility being adjusted to a portion of a subject being imaged. Therefore there is little effect upon the lines of magnetic flux and the magnetic field homogeneity, reducing distortion in an MR image. These carbon fiber instruments exhibit virtually no magnetic torsional forces when inserted into a magnetic field. This is important, for example when the instrument is a scalpel. Doped carbon fiber has minimal affect on radiofrequency fields. The instruments do not affect the homogeneity of an applied homogeneous magnetic field or an applied radiofrequency field. Doped carbon fiber exhibits a rigidity large enough to allow construction of high strength instruments such as biopsy needles. It also has the ability to retain a sharp edge, allowing construction of scalpels and cutting instruments. Doped carbon fiber surgical instruments may be used inside a magnetic field during magnetic resonance imaging, thereby allowing interactive internal images to be produced and displayed to a surgeon during surgery. A method is also disclosed for imaging a control material and then the instrument to determine the type and amount of doping agent required.

4 Claims, 3 Drawing Sheets

CARBON FIBER MAGNETIC RESONANCE COMPATIBLE INSTRUMENTS

BACKGROUND OF THE INVENTION

1. Field of the Invention

This invention relates to magnetic resonance (MR) compatible instruments, and more specifically to instruments which can be used in a magnetic field during MR imaging.

2. Description of Related Art

Magnetic resonance (MR) imaging employs large magnets for creating a homogeneous magnetic field, and gradient coils for altering the magnetic field in a uniform manner in time or space, creating magnetic field gradients. MR imaging also employs radiofrequency (RF) coils for applying an RF field to a subject to be imaged, causing the resonant nuclei within the subject to resonate and create an MR response signal. The MR response signal is used to construct an image. The degree of homogeneity of the magnetic field and the linearity of a magnetic field gradient over space are important in creating a clear, undistorted image. Interference with the RF field also reduces the quality of the created image.

The degree of magnetization the material exhibits per applied magnetic field is defined as susceptibility. A susceptibility of a material which is much different from the subject being imaged affects the magnetic field lines of flux, and hence disturbs the homogeneity of the applied magnetic field in a region near the material. This creates distortions in an MR image near the material based upon the difference in susceptibility.

The class of materials having negative magnetic susceptibilities ("$\chi$") (ranging from 0 to −1) are referred to as "Diamagnetic". The class of materials having positive susceptibilities (ranging from $\chi$=0 to +0.01) are referred to as "Paramagnetic". And finally, the class of materials which are strongly magnetic (ranging from $\chi$=+0.01 to $10^5$) are referred to as "Ferromagnetic".

Many metals are ferromagnetic and are experience torsional forces when positioned near a magnet. Since the magnetic field employed in MR imaging is large, the magnetic force can be large. If the instrument was a scalpel, only with difficulty could the surgeon manipulate it during surgery.

In addition, electrically conducting materials, such as metals, disturb and distort the radiofrequency electromagnetic fields necessary for resonance imaging. The eddy currents in these materials, usually metallic conductors of electricity create their own magnetic field which interferes with the fields used for MR imaging. If these are moved within the magnetic field, or the magnetic field is changing rapidly, currents passing through the material causes local heating. This could be a problem in a catheter which may cause burns and coagulate the tissue. Therefore, materials which are good conductors of electricity, such as metals, exhibit eddy currents should be used as little as possible.

MR imaging may be performed on may different types of subjects. The only requirement is that there should be a large amount of resonant nuclei which is capable of emitting an MR response signal.

There is currently a desire to create interactive images of internal organs of a patient during surgery. Since magnetic resonance imaging provides great detail in images of soft tissues, it is advantageous to use MR imaging. The best imaging results when surgical equipment does not interfere with the static magnetic and radio frequency magnetic fields created by the MR imaging equipment.

Typically, surgical instruments such as scalpels and biopsy needles are made of a material, usually stainless steel, which can be easily sterilized, has a great degree of rigidity, and does not cause significant adverse physiological reactions when inserted into a living subject. However, the susceptibility still is significantly different from biological tissue, and metals do exhibit eddy currents and heating.

Currently, there is a need for instruments which have the above-mentioned desirable properties, and can be used within a magnetic field during MR imaging.

SUMMARY OF THE INVENTION

Doped graphite composite material embedded in a substrate having magnetic susceptibility which closely matches that of a subject being imaged, is not ferromagnetic, compared to metal, is a poor conductor of electricity, and has the proper physical properties, such as rigidity, and the ability to maintain a sharp edge, and may be sterilized, are constructed for use within a magnetic resonance (MR) imaging system. Due to the properties of the instruments, they can be used inside the magnetic field during MR imaging, thereby allowing interactive internal images to be produced and displayed, for example, to a surgeon during surgery.

A method of constructing such instruments requires imaging a control material within a background material. The background material should have a desired susceptibility and be able to produce an MR response signal. The background material should have a susceptibility substantially equal to a portion of the subject intended to be imaged. A typical background material is water containing a dissolved paramagnetic salt, such as copper sulfate. The instrument is imaged in the same manner with the distortion of the images produced by the instrument used to determine the amount and polarity of a doping agent to be added to result in the proper susceptibility.

OBJECTS OF THE INVENTION

It is an object of the present invention to provide instruments which can be used inside a magnetic field used for MR imaging without exhibiting magnetic torsion effects.

It is another object of the present invention to provide instruments which can be used in the magnetic field of a magnetic resonance imaging system which exhibit susceptibility similar to the susceptibility of a portion of a subject being imaged and do not distort an MR image.

It is another object of the present invention is to provide instruments to be used during surgery within the magnetic field of a magnetic resonance imaging system which do not introduce artifacts in a created MR image.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

Figure 1:
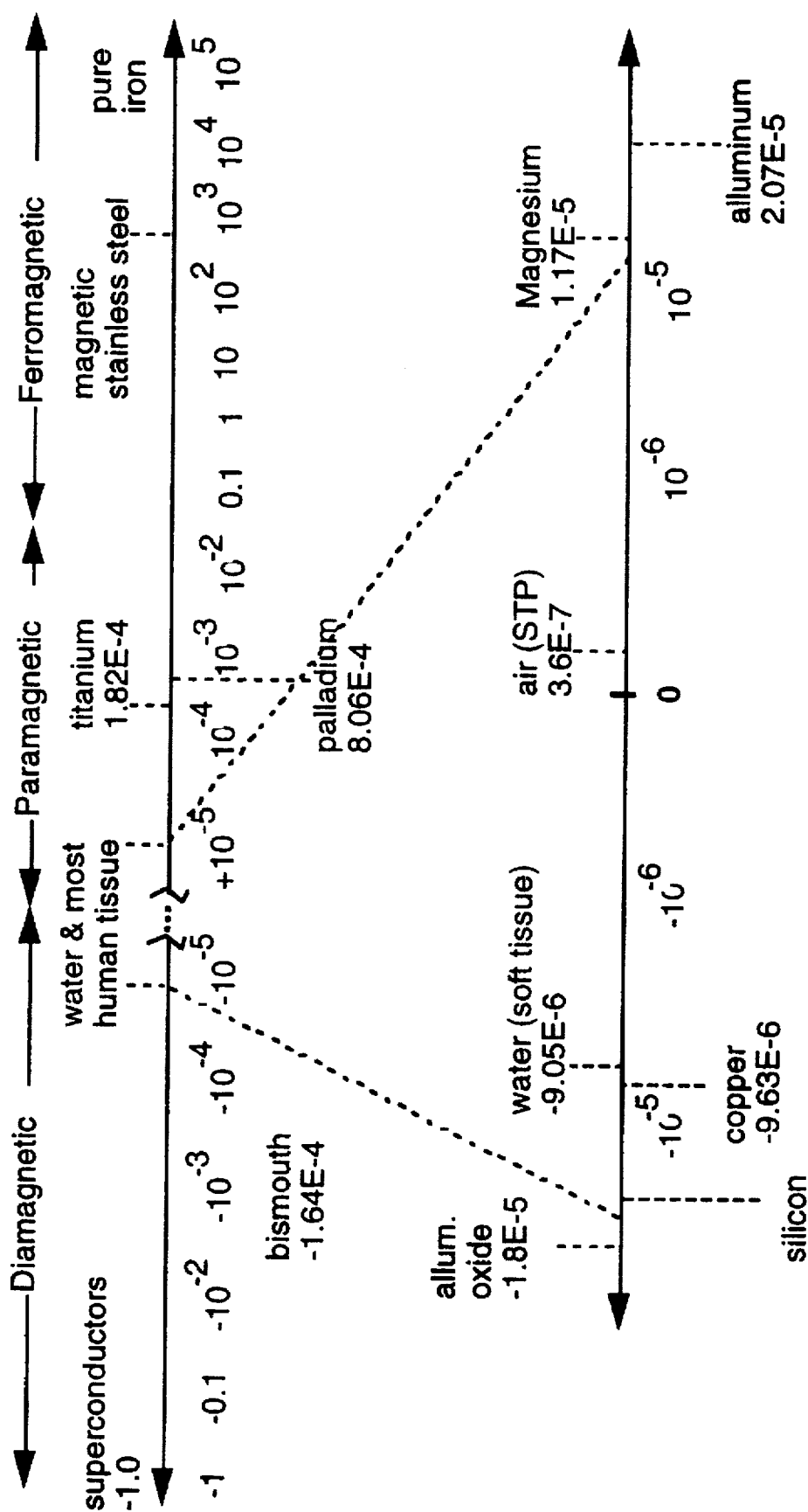
FIG. 1 is a chart showing the magnetic susceptibility of different materials.

In FIG. 1, the magnetic susceptibility in a magnetic field of different types of material are shown. Magnetic susceptibility generally ranges from −1 for superconductors to 100,000 for iron in units of parts per million (ppm.). For example, air at standard temperature and pressure is approximately $3.6 \times 10^{-7}$ ppm. Water and usually soft tissue of humans is approximately negative $9.05 \times 10^{-6}$. Deoxygenated red blood cells are approximately $-6.52 \times 10^{-6}$ ppm. Other materials are shown on FIG. 1 with their susceptibility also in parts per million. It can be seen that by combining together materials with different values of magnetic susceptibility, new materials with a different value of magnetic susceptibility may be produced. Similarly, by adjusting the amount and mixture of different materials one could adjust the susceptibility to match a material of the subject being imaged.

The subject being imaged may be a human, animal, plant, synthetic material or manufactured object.

If there are objects which need to be placed within the imaging volume during MR imaging, the objects may be matched to the susceptibility of the subject or portions of the subject. These objects may be used to hold or manipulate the subject during imaging.

In order to construct the instruments, it was determined that a composite material comprised of carbon fiber and a substrate result in an instrument approximately equal to the magnetic susceptibility of water. Since most mammalian tissue has a magnetic susceptibility approximately equal to that of water, this would be a good starting point for instruments used while imaging this type of tissue.

The carbon fiber is made from graphite which is a moderate conductor of electricity. Carbon fiber does not exhibit any rigidity by itself, but when combined with an appropriate binding material such as epoxy resin, a composite material of considerable strength is produced. The susceptibility of graphite single crystals, carbon fibers, is anisotropic. This means that it has one magnetic susceptibility ($-5.95 \times 10^{-4}$) for directions perpendicular to planes of the carbon atoms, and a second magnetic susceptibility ($-0.085 * 10^{-4}$) for directions parallel to the planes of carbon atoms.

Substrate

The substrate may be an epoxy which is poured or molded in with the carbon fiber. The final result of the epoxy and carbon fiber exhibits a rigidity which is acceptable for many different instruments. By selecting an optimum relative ratio of carbon fiber to substrate, maximum durability results. The preferred mix is about 60% carbon fiber to 40% substrate by weight.

Other resins may be used with the carbon fiber as a substrate.

Other Substrates

Other substrates, such as thermosetting plastics, other polymers or composites may be employed if they meet the physical requirements of the instrument to be used, such as rigidity, Young's Modulus, fracture characteristics. These must be doped to match the subject or portion of the subject being imaged, such as by the method discussed below.

For a more detailed discussion of conventional construction of carbon fiber composites, and their physical properties, please refer to chapters 1 and 6 of "Carbon Fibers, Formation, Structure and Properties" by Leighton H. Peebles, CRC Press, Boca Raton, Fla. (1995).

Doping

Since the carbon fiber/substrate composite exhibits a susceptibility slightly more negative than that of human tissue and water, doping with a doping agent having a more positive magnetic susceptibility is required to match the susceptibility to that of human tissue, when imaged. Using a material with a very high positive magnetic susceptibility such as iron in the form of iron oxide, would require very little iron oxide to be added to the substrate/carbon fiber to raise the magnetic susceptibility to that of water. It is to be understood that any material with a greater magnetic susceptibility being more positive than water may be used. The lower the value of the magnetic susceptibility of the doping agent, the greater the amount of the doping material required.

For example, a doping agent, such as iron oxide powder ($Fe_2O_3$), also known as hematite, which has a positive magnetic susceptibility of $1.46 \times 10^{-3}$ may be used during construction of an instrument to be used in a magnetic field. By incorporating a controlled amount of this material, or other doping agent, the magnetic susceptibility of the instrument being constructed may be adjusted over a wide range to match the magnetic susceptibility of the subject being imaged.

The presence of an object within an imaging volume with a different magnetic susceptibility causes a characteristic distortion of the MR image which reveals both the magnitude and the sign of the discrepancy. This discrepancy is the difference between the magnetic susceptibility of the object, and that of the subject being imaged.

In order to properly match the susceptibility of the instrument to that of the subject, the doping agent may be incrementally added, and a susceptibility match tested at different doping levels to determine an optimum doping concentration.

Figure 3:
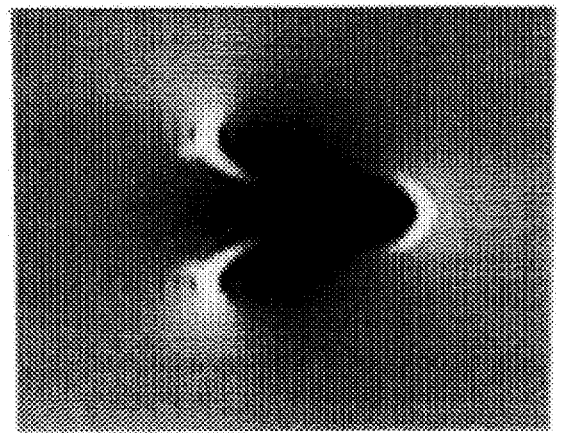
FIG. 3 is an MR image of a cylinder constructed of bismuth as the control material in water as a background material, showing the distortion due to differences in magnetic susceptibility.

In FIG. 3, an image of a cylindrical object constructed of Bismuth having a magnetic susceptibility difference $\Delta_\chi = -155$ ppm less than a surrounding material. Notice that it produces an arrow shaped artifact pointing to the right. The direction in which the arrow artifact is pointing indicates the sign of the difference. The length of the "stretching" indicates the magnitude of the magnetic susceptibility difference.

Figure 4:
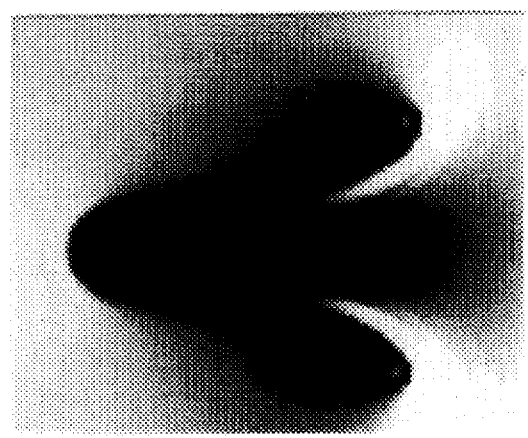
FIG. 4 is an MR image of a cylinder constructed of titanium as the control material in water as a background material, showing the distortion due to differences in magnetic susceptibility.

Similarly, FIG. 4 is an image of a spherical object constructed of Titanium having a magnetic susceptibility difference $\Delta_\chi = 191$ ppm greater than a surrounding material. Notice that it produces an arrow shaped artifact pointing to the left.

Therefore, instruments intended for use in a magnetic field may be constructed by the following steps:

1. Select a background material having a magnetic susceptibility approximately equal to that of a subject, or portion of a subject intended to be imaged.

2. Select a control material formed in a known shape, having a different known magnetic susceptibility difference, a control difference ($\Delta_\chi$) with a known polarity with respect to the background material.

3. Performing magnetic resonance (MR) imaging on the background material and control material to result in a distorted MR control image, which will have artifacts.

4. Identifying the size, shape of the artifact, and the direction in which the artifacts are deformed, and the degree of distortion.

5. Constructing an instrument from a material.

6. Imaging the instrument within the background material to create an instrument MR image.

7. If the image deviation is smaller than a predetermined minimum threshold value, the instrument is acceptable for use in a MR imaging system, stop.

8. If the image deviation is larger than a predetermined minimum threshold value, estimate the magnitude of the image distortion relative to the control image.

9. Estimating an instrument susceptibility difference ($\Delta_\chi$) and polarity for the instrument from the instrument MR image and the control MR image.

10. Computing an amount of a doping agent which would cause the instrument susceptibility difference ($\Delta_\chi$) to become substantially zero.

11. Either adding the computed amount of doping agent to the instrument, or constructing another instrument with this amount of doping agent to result in an instrument which may be used in MR imaging which would distort the image very little.

Conventional image processing techniques may be employed to determine the degree of distortion of the images. This may take into account not only the spatial offset of a pixel from where it should be, but the relative intensity of pixels of the distorted image, relative to what their intensity in the undistorted image.

In order to calculate the amount of doping agent needed, the degree of distortion is a required, the polarity offset (either positive or negative), and the susceptibility of the doping agent are required. This should result in an amount required per unit volume, and is adjusted for the volume of the instrument.

Please note that if the control object is constructed with the same dimensions as the instrument, the distortion of the images created may be more easily compared.

Also, for instruments with anisotropic composites, this process may be repeated with different instrument orientations with respect to the magnetic field, and an averaging of the doping agent required for different orientation be used. This would cause a more consistent image to be produced with different instrument orientations within the magnetic field.

If the magnetic susceptibility of the substrate/carbon fiber composite changes during hardening, this must be taken into account when adding the doping agent.

In constructing an instrument according to the above discussed method, bismuth is a material which has a very large negative susceptibility, and may be used for the control material. Almost any background material employed will be positive with respect to bismuth, and produce an MR image indicating a strongly negative magnetic susceptibility with respect to the background material.

When doping the composite instrument, care must be taken in order to insure that the magnetic susceptibility of the instrument is uniform so as not to cause localized magnetic field distortions.

Figure 2:
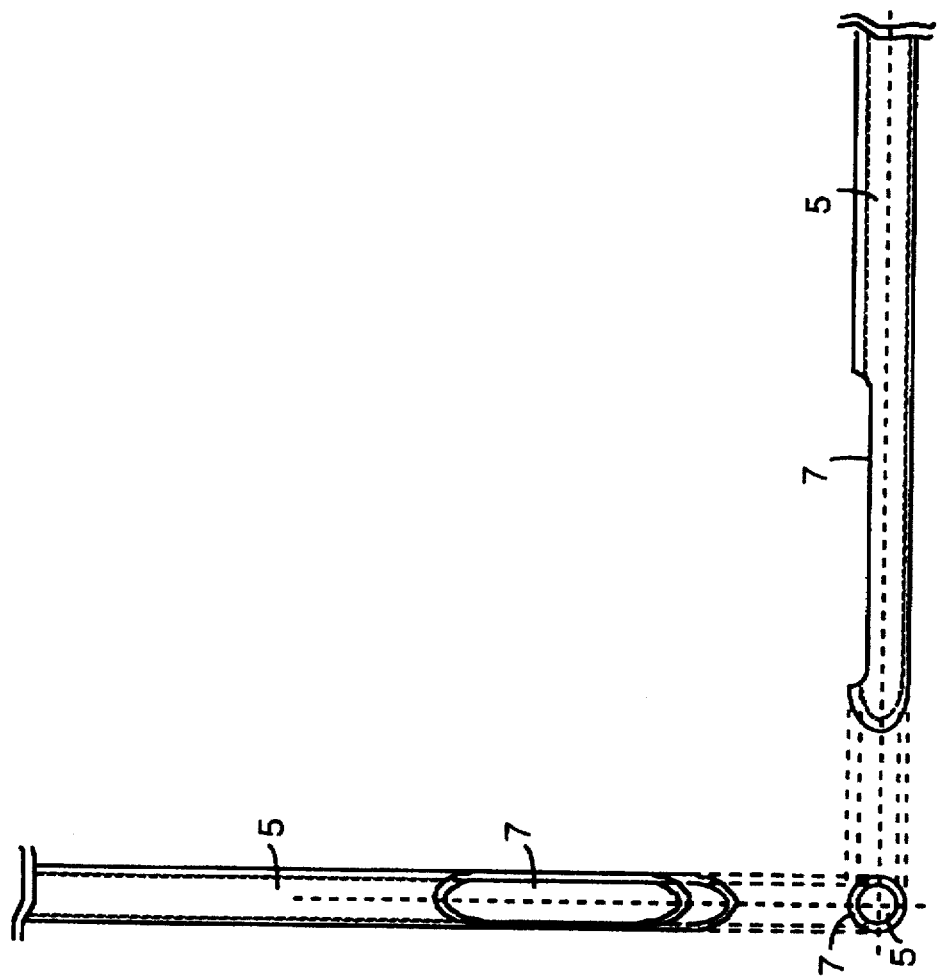
FIG. 2 is a plan view of a biopsy needle constructed of a material having a magnetic susceptibility close to human tissue according to the present invention.

In FIG. 2 a carbon fiber composite brain biopsy device is shown. The biopsy needle has a central opening 5 passing though the length of the device. The biopsy device is constructed of a high-strength carbon fiber composite material. The biopsy needle is inserted into a patient by penetrating the patient's brain tissue in order to retrieve a small sample which is collected by side opening 7 and central opening 5. The biopsy is removed from the patient and extracted for tests. In order to reduce the invasiveness of the procedure, the biopsy needle is made as thin as possible. In order to make the biopsy needle thin, it must be constructed of a material having a great degree of strength and rigidity. In this case, the device may have a diameter of 1–3 mm, with a wall thicknesses ranging from 0.29 mm–0.5 mm.

The composite material used in these instruments to be used during surgery should be one which can be sterilized and that is bio-compatible. A bio-compatible material is one which is not toxic and does not cause significant adverse physiological reactions. For example, copper is not bio-compatible. When copper is introduced into mammalian tissue, copper ions are released causing tissue toxicity.

Any surgical instrument which may be required in surgery, such as, but not limited to: a scalpel, biopsy needle, optical fiber guide, retractor, clamp, syringe, catheter and scissors, may be fabricated according to the requirements set forth for the biopsy needle and scalpel above.

While several presently preferred embodiments of our novel invention has been described in detail, many modifications and variations will now become apparent to those skilled in the art. It is our intent to be limited only by the scope of the appending claims and not to the specific details and examples presented above for explanation purposes.

What is claimed is:

1. A method for constructing instruments intended for use during magnetic resonance (MR) imaging of a subject having a predetermined magnetic susceptibility, comprising the steps of:

a) selecting a background material having a magnetic susceptibility substantially equal to a portion of a subject intended to be imaged;

b) selecting a control material having a known magnetic susceptibility difference, ($\Delta_\chi$) from that of the background material;

c) obtaining a magnetic resonance (MR) image of the control material of a known shape embedded within the background material to result in a distorted control image caused by the difference in susceptability of the materials;

d) measuring the size and direction of distortion of the control image with respect to the shape of the control material shape;

e) determining the size of distortion of the control image per unit of susceptibility difference ($\Delta_\chi$);

f) equating a direction of control image distortion with the polarity of magnetic susceptibility difference;

g) constructing an instrument from a composite material;

h) imaging the instrument within the background material to create an instrument image having distortion;

i) measuring a size and a direction of distortion of the instrument image;

j) estimating a susceptibility difference and polarity between the instrument and background material from the instrument image and the computed distortion per unit susceptability difference;

k) computing an amount of a doping agent of a known susceptability to be added to the instrument which would cause the susceptibility difference to become substantially zero; and l) adding the computed amount of doping agent to the instrument to result in an instrument which may be used in MR imaging which would distort the image very little.

2. The method for constructing instruments of claim 1 further comprising, after step "l", the step of:

repeating steps "h"–"l" until the magnetic susceptibility of the instrument substantially matches that of the subject desired to be imaged.

3. A method for constructing instruments intended for use during magnetic resonance (MR) imaging of a subject having a predetermined magnetic susceptability, comprising the steps of:

a) selecting a background material having a magnetic susceptibility substantially equal to a portion of a subject intended to be imaged;

b) selecting a control material having a known magnetic susceptibility difference, ($\Delta_\chi$) from that of the background material;

c) obtaining a magnetic resonance (MR) image of the control material of a known shape embedded within the background material to result in a distorted control image caused by the difference in susceptability of the materials;

d) measuring the size and direction of distortion of the control image with respect to the shape of the control material shape;

e) determining the size of distortion of the control image per unit of susceptibility difference ($\Delta_\chi$);

f) equating a direction of control image distortion with the polarity of magnetic susceptibility difference;

g) constructing an instrument from a composite material;

h) imaging the instrument within the background material to create an instrument image having distortion;

i) measuring a size and a direction of distortion of the intrument image;

j) estimating a susceptibility difference and polarity between the instrument and background material from the instrument image and the computed distortion per unit susceptability difference;

k) computing an amount of a doping agent of a known susceptability to be added to the instrument which would cause the susceptibility difference to become substantially zero; and l) constructing another instrument with this amount of doping agent to result in an instrument which may be used in MR imaging which would cause less distortion in an MR image.

4. The method for constructing instruments of claim 3 further comprising, after step "l", the step of:

repeating steps "h"–"l" until the magnetic susceptibility of the instrument substantially matches that of said subject, indicating that the instrument is now acceptable for use in a MR imaging system.

* * * * *